United States Patent [19]

Kunsch

[11] 4,442,884
[45] Apr. 17, 1984

[54] PROCESS AND APPARATUS FOR AUTOMATIC AND CONTINUOUS MEASUREMENT OF THE SHEARING RESISTANCE OF GREEN SAND USED IN MODERN MOLDING MACHINES

[75] Inventor: Robert Kunsch, Rueil Malmaison, France

[73] Assignee: Regie Nationale des Usines Renault, Boulogne-Billancourt, France

[21] Appl. No.: 416,967

[22] Filed: Sep. 13, 1982

[30] Foreign Application Priority Data

Sep. 11, 1981 [FR] France .................. 81 17244

[51] Int. Cl.³ .................. B22D 46/00; B22C 15/02; B22C 19/00
[52] U.S. Cl. .................. 164/456; 164/150; 164/207
[58] Field of Search .......... 164/4.1, 456, 150, 157, 164/200, 201, 202, 210, 207

[56] References Cited

U.S. PATENT DOCUMENTS 3,335,787 8/1967 Dietert .................. 164/150
3,373,977 3/1968 Dietert .................. 259/154

FOREIGN PATENT DOCUMENTS 2937473 2/1981 Fed. Rep. of Germany .
1389730 9/1968 France .

*Primary Examiner*—Gus T. Hampilos
*Assistant Examiner*—Jerold L. Johnson
*Attorney, Agent, or Firm*—Oblon, Fisher, Spivak, McClelland & Maier

[57] ABSTRACT

Process for automatically measuring the shearing resistance of green sand used in a repetitive sand molding process using pattern plates, and for using the measurements in such a way as to modulate the various parameters of the process in which a measuring ring is placed upon one of the pattern plates. The measuring ring has an opening and stress gauges fastened within narrowed sections of said measuring ring on either side of said opening. The gauges are connected electrically through the pattern plate to an electronic measurement and operation device within which various physical measurements are computed, including the shearing resistance of the test sample of sand compressed within said opening. The result of said measurements is processed by a computer to determine the magnitude of modulations to be made, particularly that pertaining to the replenishment of agglomerating agents for the recycled sand.

6 Claims, 3 Drawing Figures

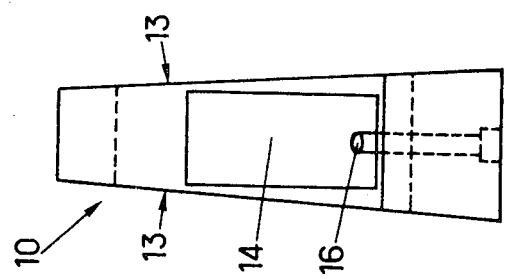
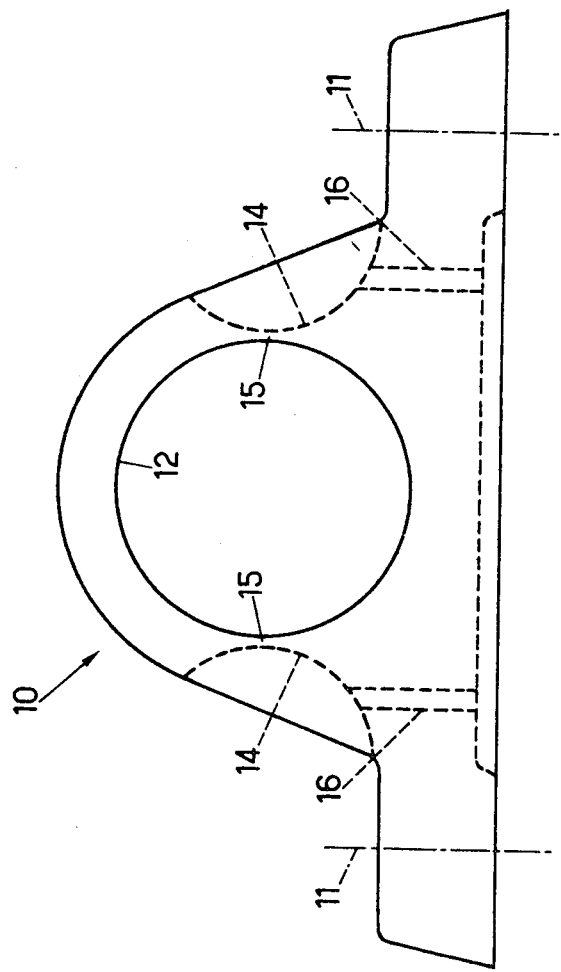

PROCESS AND APPARATUS FOR AUTOMATIC AND CONTINUOUS MEASUREMENT OF THE SHEARING RESISTANCE OF GREEN SAND USED IN MODERN MOLDING MACHINES

BACKGROUND OF THE INVENTION

1. Field of the Invention

The invention relates to sand molding, and more particularly to modern, automatic, repetitive, high-speed molding processes.

2. Description of the Prior Art

A well known sand molding process consists of forming essentially parallelopiped blocks by compressing sand in a horizontal press between a front pattern plate which opens and a back pattern plate which exerts pressure. In this process, the blocks are assembled into a continuous horizontal column as they leave the press, forming a complete mold impression at each joint between blocks, which will then enable metal to be poured repeatedly into the various impressions. The blocks continue to advance, while the pieces cool, up to an end station where the sand is removed. In each operating cycle, sand is projected vertically and at high speed into the press between the closed front plate and the withdrawn back plate before the pressure is applied.

The sand used is molding sand called green sand, a material composed of silica grains mixed with a clay called bentonite, powdered charcoal, and water. By appropriate mixing, each solid grain is coated with a thin film of suitably hydrated clay in order to impart the necessary adhesive power under a high forming pressure, generally on the order of 10 kg/cm$^2$.

Like any molding sand, this sand must meet conflicting requirements, since it must be sufficiently fluid to be able to be easily packed around all of the details of the pattern plates, while at the same time being sufficiently stiff not to collapse after packing nor to lose shape after separation from the pattern plates. It must also exhibit good cohesion, particularly a shearing resistance high enough to resist the stresses of molding, such as the hydrostatic pressure of molten metal, the thermic shocks at the moment of pouring, and the stresses due to the contraction of the metal in the process of solidification. Moreover, it must be able to be broken for the extraction of the pieces without too much difficulty.

Modern molding processes such as the one described above are even more demanding on the quality of the sand due to the absence of any frame, which thus necessitates a greater self-cohesion of the blocks, the high pressure exerted on the sand in the joint planes of the lead blocks, which must push back the whole column and, finally the fact that the sand removal operation itself must be automatic and take place at high speed. In each case, an optimal quality of sand must be set and it is necessary to monitor this quality to ensure that it remains within the narrow and precise limits thus defined.

The usual methods for monitoring the quality of the sand consist of drawing off a sample of non-packed sand, i.e., from the hopper of the machine, forming a test cylinder (5 cm×5 cm) in an outside laboratory apparatus, compressing it at 10 kg/cm$^2$, and shearing it on a special machine. Depending on the result of this measurement, the replenishment of agglomerating agents, or bentonite clay, is adjusted as a function of the observed fluctuations from the set limits. These measurements are repetitive, but as a result of the process used the measurement speed is always slow and rarely exceeds more than two measurements per hour, which nevertheless requires a full-time operator and imposes a great lag between the moment of sampling and the moment at which the result of the measurement is finally known.

This known process permits the above demand for constancy of sand quality to be met only in a way that is approximate. In addition, the check covers only the quality of the sand per se, prior to packing, and not the real conditions in which it is found inside the block.

SUMMARY OF THE INVENTION

The object of the invention is to eliminate the foregoing drawbacks by providing a process and apparatus for measuring, as rapidly and automatically as possible, the quality of the sand per se as well as the quality of its packing within each block.

The invention consists of fastening onto one of the pattern plates, preferably the back one, a measuring ring having a central hole, preferably one whose axis is parallel to the pattern plate and preferably parallel to the direction from which the sand is blown (i.e., generally vertically) with a narrowed section along its two lateral edges containing a stress gauge electrically connected across the support and the pattern plate to an outside measuring apparatus. This ring is defined by two planes, either parallel or preferably, slightly tapered in the direction of withdrawal of the mold, so that when the pattern plate is drawn away from the block, the ring performs a double shearing of the cylinder of sand contained inside its hole, said sand having been compacted by the normal process of producing the block under the normal conditions prevailing within. The signals provided by the stress gauges are analyzed electronically to give the shearing resistance and processed by computer to govern various parameters, particularly instructions for adjustment of the replenishment of agglomerating agents and for adjustment of the pressure exerted by the press.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein:

FIGS. 2 and 3 are respectively an elevation and a side view of the measurement ring.

DETAILED DESCRIPTION OF THE PREFERRED EMBODIMENTS

Figure 1:
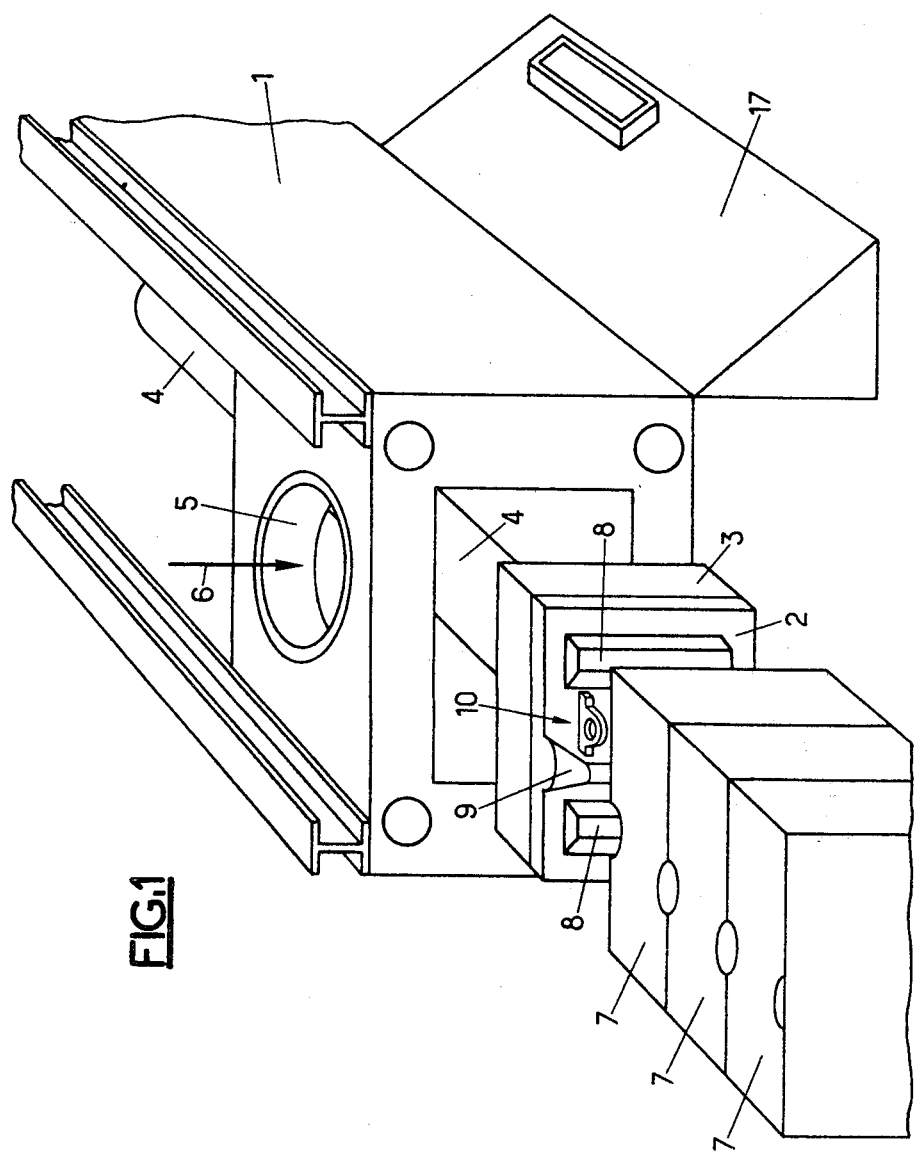
FIG. 1 is a partial perspective of the press and of its back pattern plate in an out position.

In FIG. 1 can be seen press 1 having back pattern plate 2 borne by plate 3 of the press, plate 3 being integral with shank 4. Sand is blown through opening 5 in the direction of arrow 6. One end of the column of blocks 7 can also be seen.

In a known fashion, pattern plate 2 comprises protrusions 8 corresponding to the shape of the piece to be molded, up to the joint plane (shapes beyond this plane are carried on the other pattern plate, which is not shown), as well as protrusion 9 intended to form the pouring hole and pouring channel (direct or from a source).

In accordance with the invention, a measurement ring 10, shown in detail in FIGS. 2 and 3, is fastened onto pattern plate 2 in an appropriate spot between the protrusions 8 and 9, preferably in the core of the block.

This ring is advantageously in the shape of a journal bearing having a base so as to enable it to be conveniently fastened to pattern plate 2 using screws passing through holes 11 in its base. The ring includes a hole 12 (e.g., 50 mm diameter) the axis of which is parallel to the direction of arrow 6 (e.g., generally vertical). The body of the ring, made of wear resistant steel, preferably 35CD4T4 steel, is defined by two planes 13 essentially perpendicular to pattern plate 2 but preferably tapered slightly in the direction of withdrawal, as shown in FIG. 3. Two lateral millings 14 (e.g., cylindrical, as shown in the figures) have the effect of reducing the section of the lateral branches of the ring—which extend in the direction in which the pattern plate is extracted—down to a small section 15 (e.g., on the order of 1.5 mm in thickness). At the point of maximum reduction, which corresponds to the point at which tangents to hole 12 are parallel to the direction of shank 4 of the press, stress gauges (not shown) are fastened in the bottom of millings 14 and are coupled by a Wheatstone bridge with thermic compensation gauges in the usual manner and connected electrically by cables passing through ring 10, via holes 16, and through pattern plate 2 and plate 3, via appropriate holes, so as to reach the measuring and operating apparatus 17 by means of flexible connections (not shown).

When sand is compacted between the two pattern plates, sand also fills hole 12 of ring 10 and is there compacted at the pressure existing at that spot. When the pattern plate is withdrawn by retraction of shank 4, the ring draws with it the cylinder of sand it contains, separating said sand cylinder from the rest of the block by a double shearing along planes 13. The tapering of these two planes facilitates this separation by avoiding the imposition of parasitic stresses which would affect the measurement. The two millings 14 are preferentially filled with a filler material designed to protect the stress gauges from the sand while at the same time eliminating any counter-taper.

The shearing resistance of the cylinder of sand along the two shearing planes 13 is thus measured precisely by the sum of the tensions of the two sections 15, which are measured by the stress gauges, and which are related to the sum of the two sections and of the cylinder of sand.

The indentation made by the ring in the block is not important since it does not communicate with the other impressions or with the pouring hole. On the other hand, by virtue of the orientation selected for the ring, the cylinder of sand which remains in hole 12 of the ring is removed in the next molding cycle by the projection of sand blown into the press in direction 6. The sand thus flushed downward by blowing pressure mixes with and adheres to the rest of the sand in the following pressing cycle.

With each cycle of formation of blocks 7, the invention thus provides a precise and instantaneous measurement of the shearing resistance of the cylinder of sand under the compacting pressure actually present within the block.

These various measurements, succeeding each other at the speed of the press, may advantageously be monitored by an electronic computer, which computes the shearing resistance in the appropriate units as well as various required data and stores this data in memory in order to carry out a periodic computation (e.g., every 100 samplings) of statistical parameters, such as average and scattering, which are compared with the preset tolerances, and to provide the necessary instructions for manual or automatic correction of the replenishment of agglomerating agents to successive loads of sand sent to the hopper of the press. As long as the press works at constant pressure, variations in the measurements can only be ascribed to variations in the composition of the sand.

Moreover, if the properties of the sand used are known, the process of the invention further enables one to monitor the quality and development of packing in the core of the mold, and to regulate accordingly the pressure exerted by the press. It also enables individual monitoring to check that each mold actually receives the correct pressure, with an instantaneous warning in the event of any lapse.

The invention thus eliminates the need for employment of a monitor while furnishing instantaneous indications concerning the various adjustments to be made, either manually or automatically, in order to achieve perfect manufacturing uniformity enabling production of quality castings with a minimum of rejects.

Finally, the invention clearly can be very simply adapted to existing equipment.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for automatically measuring the shearing resistance of green sand used in a repetitive sand molding process, comprising the steps of:
    introducing green sand in a first direction between opposing pattern plates of a mold press;
    positioning a measuring ring on the pattern face of one of said pattern plates, said ring including a central opening and stress gauges fixed to sections of said ring, said sections being narrower than the remainder of said ring;
    electrically connecting said stress gauges to electronic means for determining stresses measured by said rings;
    forming a sand block in said mold press, the sand block including a sand cylinder formed in said central opening of said ring;
    separating said pattern plates from the sand block to shear the cylinder from the block; and
    using said electronic means to determine the shearing resistance of said sand cylinder.

2. The process of claim 1 wherein said ring is fixed to a back plate of said pattern plates, and wherein said central opening is oriented with the axis of said ring parallel to said first direction, whereby the sand ring formed in each sand block forming cycle is removed by the introduction of green sand in a following cycle.

3. The process of claims 1 or 2 including the steps of comparing said measured stress resistance with a desired stress resistance and modifying at least one of the sand composition and the press pressure as a function of said comparison.

4. A device for automatically measuring the shearing resistance of sand used in a repetitive sand molding process in a sand molding press having a front pattern plate, a back pattern plate, means for introducing green sand between said plates in a first direction prior to each molding cycle, and means for moving one of said plates in a second direction transverse to said first direction, said device comprising:

a ring including an integral base, said ring having a central opening, said base being fixed to a pattern face of said moving one of said plates with the axis of said central opening extending perpendicular to said second direction and parallel to said first direction;

circumferentially opposing recesses formed in an axially central outer surface portion of said ring to form narrow ring sections, said recesses being circumferentially positioned at points where a tangent to said central opening extends parallel to said second direction;

stress gauges formed at the bottoms of said grooves and in contact with said narrow ring sections;

electronic means associated with said stress gauges for determining stress as a function of electric signals from said stress gauges; and means for providing said signals from said stress gauges to said electronic means.

5. The device of claim 4 wherein the axial surfaces of said ring are defined by planes tapering toward one another relative to said second direction as said planes extend away from said base.

6. The device of claims 4 or 5 including:

filler means filling said grooves; and holes defined in said base, said holes house said means for providing signals.

* * * * *